United States Patent
Mossman et al.

(10) Patent No.: US 6,267,559 B1
(45) Date of Patent: Jul. 31, 2001

(54) APPARATUS AND METHOD FOR REDUCING POWER CONSUMPTION IN A PERISTALTIC PUMP MECHANISM

(75) Inventors: John Archie Mossman, La Mesa; Darin Kent Woolf, Vista, both of CA (US)

(73) Assignee: Alaris Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/470,318

(22) Filed: Dec. 21, 1999

(51) Int. Cl.[7] .................................................. F04B 49/06
(52) U.S. Cl. ............................................................. 417/44.1
(58) Field of Search .................................. 417/44.1, 474, 417/471, 465, 466

(56) References Cited

U.S. PATENT DOCUMENTS 6,106,249 * 8/2000 Barak ................................... 417/474

* cited by examiner

Primary Examiner—Teresa Walberg
Assistant Examiner—Vinod D Patel
(74) Attorney, Agent, or Firm—Pennie & Edmonds LLP (57) ABSTRACT

The present invention utilizes a torque compensation system and a power control feedback system to reduce power consumption in a linear peristaltic pump. The linear peristaltic infusion pump includes an electric motor, which is connected to a cam shaft with multiple cams positioned thereon. Numerous elongate fingers cooperate with the cams to partly occlude an intravenous drip tube at multiple points along the tube's path. A torque compensation system and power feedback control system reduce the overall power consumption of the pump. A torque compensation cam positioned on the cam shaft, in combination with a torque compensation cam follower and a mechanical spring assist the motor while it is working against a rising cam follower. The power feedback control system comprises a controller which optimally adjusts the power supplied to the drive means so as to reduce overall power consumption of the pump.

12 Claims, 7 Drawing Sheets

APPARATUS AND METHOD FOR REDUCING POWER CONSUMPTION IN A PERISTALTIC PUMP MECHANISM

TECHNICAL FIELD

The present invention relates generally to linear peristaltic pumps and in particular to a torque compensation system and a power control feedback system, used to reduce power consumption in a linear peristaltic pump.

BACKGROUND OF THE INVENTION

Various devices have been developed to improve the administration of intravenous (IV) fluids to patients in a controlled and accurate manner. One such device, is the peristaltic infusion pump. The peristaltic pump mechanism typically operates a series of fingers or rollers which deform and occlude a resiliently deformable IV drip tube at multiple points sequentially along the tube's length. These occlusions form a wave like motion which forces the IV fluid under positive pressure along the tube. The flow rate and hence dosage of the liquid is controlled by adjusting the speed of the pumping mechanism.

The finger type peristaltic pump typically comprises a motor, a set of gears, a cam shaft, a plurality of cams and a plurality of cam following fingers as per the assignee's invention described in U.S. Pat. No. 5,741,121. The finger type peristaltic pump is especially well suited for medical applications as only the tube comes into contact with the fluid, eliminating the risk of the pump contaminating the fluid, or the fluid contaminating the pump. Another advantage for medical applications is that fragile blood cells are not damaged by the pump.

An infusion pump occasionally needs to operate on Direct Current (DC), and not on Alternating Current (AC), such as for example in emergencies or where a battery needs to be used where mains power is not accessible or available. In these situations, power consumption is vital.

The fingers or cam followers of the finger type peristaltic pump are typically driven by rotating cams with varying profiles. In order to maintain a constant and accurate fluid flow and to reduce power consumption as well as to reduce audible noise and vibration at the motor, it is desirable that the cams on the shaft, rotate smoothly at a controlled speed. As the cam followers contact and apply a force to the cams, the cams in turn apply a tangential force to the shaft which produces a rotational torque tending either to aid or to impede the rotation of the shaft. This torque therefore causes variations in load presented to the motor. Such load changes affect the power consumption of the motor and may in turn adversely impact audible noise and the accuracy with which the pump delivers fluid.

NATWICK (U.S. Pat. Nos. 5,357,827 and 5,488,769) teaches an infusion pump incorporating a torque compensating cam. The purpose of the torque compensating cam in NATWICK, is however to aid in keeping the motor of the pump running at a constant rate, and not to aid power consumption.

Many high speed devices and machines make use of drive shafts to run various power take-off devices. The drive shafts of these machines experience variable torque at each torque load point where a power take-off device is connected to the shaft. In high speed engines, such as for example internal combustion engines, variable torque can cause angular twisting of the drive shaft which leads to fatigue and wear on both the drive shaft and the driven components. It is well known to use compensation cams in such applications to reduce the torque applied to the engine shaft (see U.S. Pat. Nos. 5,040,500 and 5,544,537). The purpose of using compensation cams in such applications is to prolong the life of the cam shaft by reducing vibration and wear, and not to reduce power consumption.

SUMMARY OF THE INVENTION

According to the invention there is provided a linear peristaltic infusion pump which includes a drive means, such as an electric stepper motor, which is operatively connected to a cam shaft with multiple cams positioned thereon. Numerous cam followers are, in turn, operatively connected to each corresponding cam. A plurality of elongate fingers engage corresponding cam followers and are capable of at least partly occluding an intravenous drip tube at multiple points along the tube's path. Most importantly, the pump also includes a power reduction system.

In one embodiment of the invention, the power reduction system comprises a torque compensation system. The torque compensation system comprises a torque compensation cam positioned on the cam shaft, in combination with a torque compensation cam follower which cooperates with the torque compensation cam. An energy storage element, such as a mechanical spring, forcibly engages the torque compensation cam follower against the torque compensation cam to assist the motor while it is working against a rising cam follower. The torque compensation system therefore decreases torque produced at the motor reducing power consumption of the pump.

In another embodiment of the invention, the power reduction system also includes a power feedback control system. The power feedback control system comprises a variable output power supply, which controls the power supplied to said motor, a transducer for measuring excess power in the system and a controller. The controller is capable of dynamically adjusting the variable output power supply based on the measured excess power and a predetermined desired power. The predetermined desired power is set by software control for a specific pumping rate set by the user of the pump. The power feedback control system optimally adjusts the power supplied to the drive means so as to reduce overall power consumption of the pump.

According to the invention there is further provided a method of reducing the power consumption of a peristaltic infusion pump by utilizing the above mentioned feedback control system. The user sets a desired pumping rate, from which a desired power value is determined. Using a sensor or a transducer, any excess power drawn by the motor caused by torque loading is measured. The excess power value in combination with the predetermined desired power is used by a controller to form a new power value which is fed into the variable power supply so as to adjust the power supplied to the motor.

BRIEF DESCRIPTION OF THE DRAWINGS

For a better understanding of the nature and objects of the invention, reference should be made to the following detailed description taken in conjunction with the accompanying drawings, in which.

DESCRIPTION OF THE INVENTION

Figure 1:
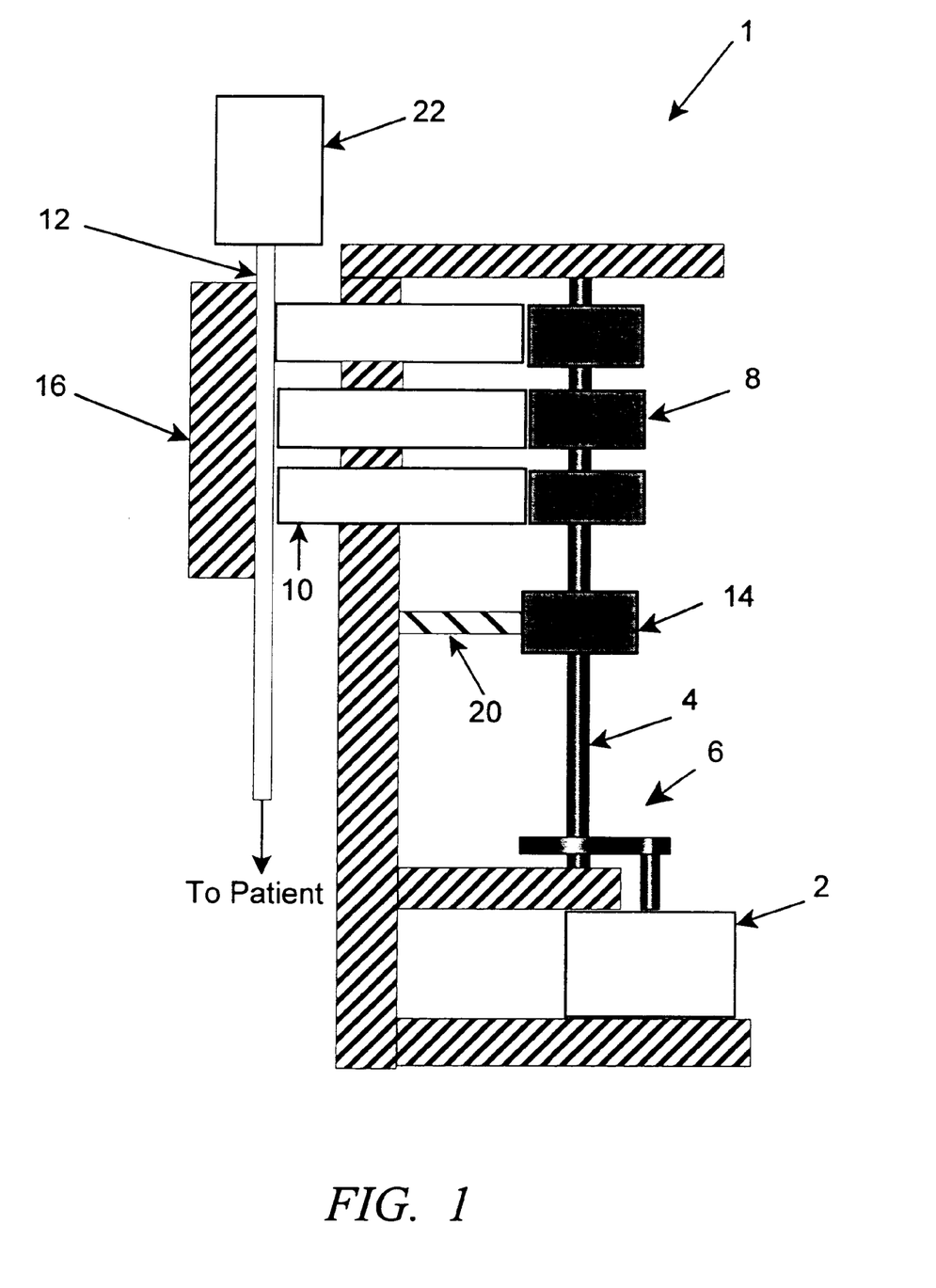
FIG. 1 is a schematic side view of an infusion pumping system according to one embodiment of the invention.
Figure 2:
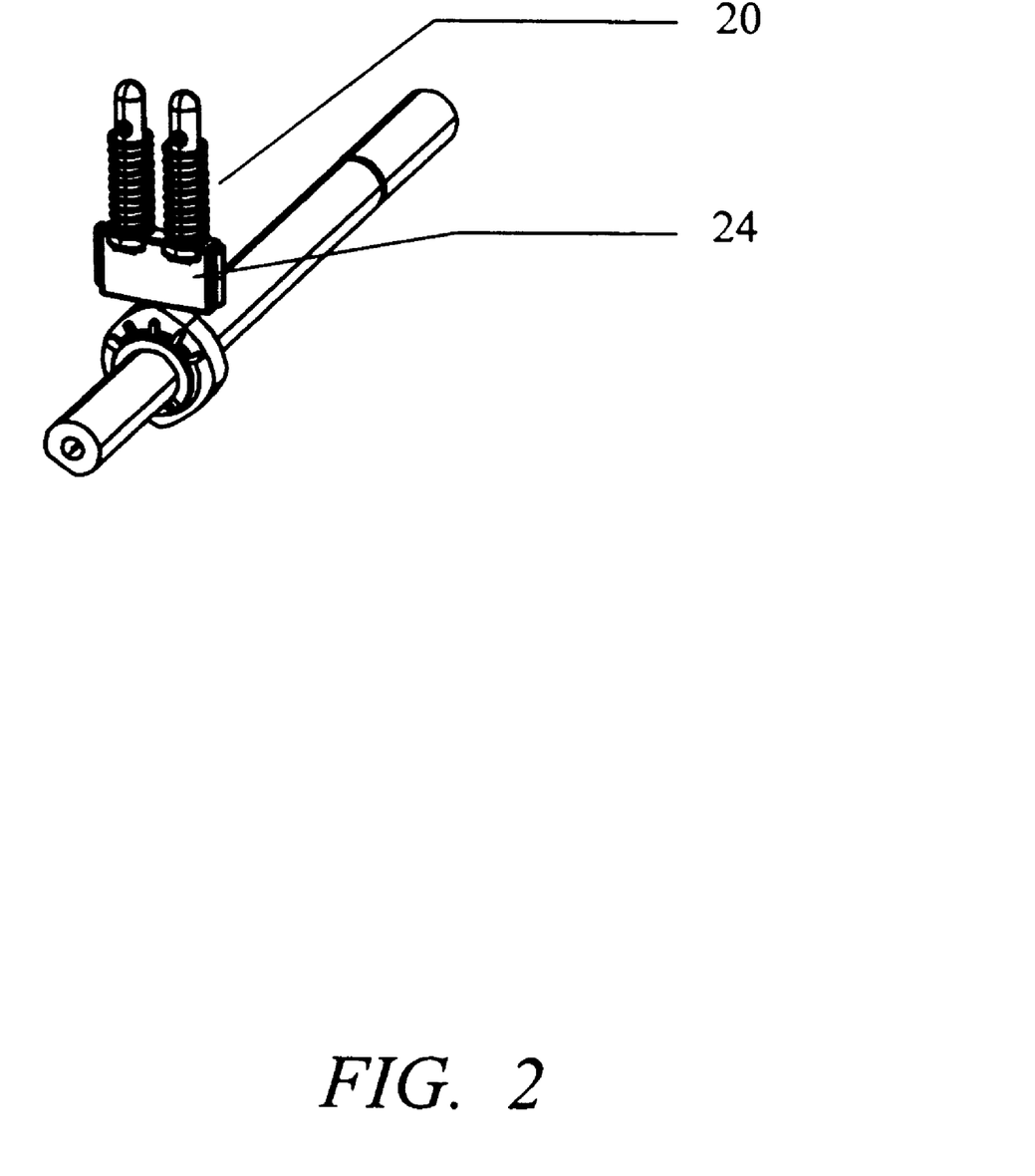
FIG. 2 is a perspective view of a compensation cam, without a housing, according to one embodiment of the invention
Figure 3:
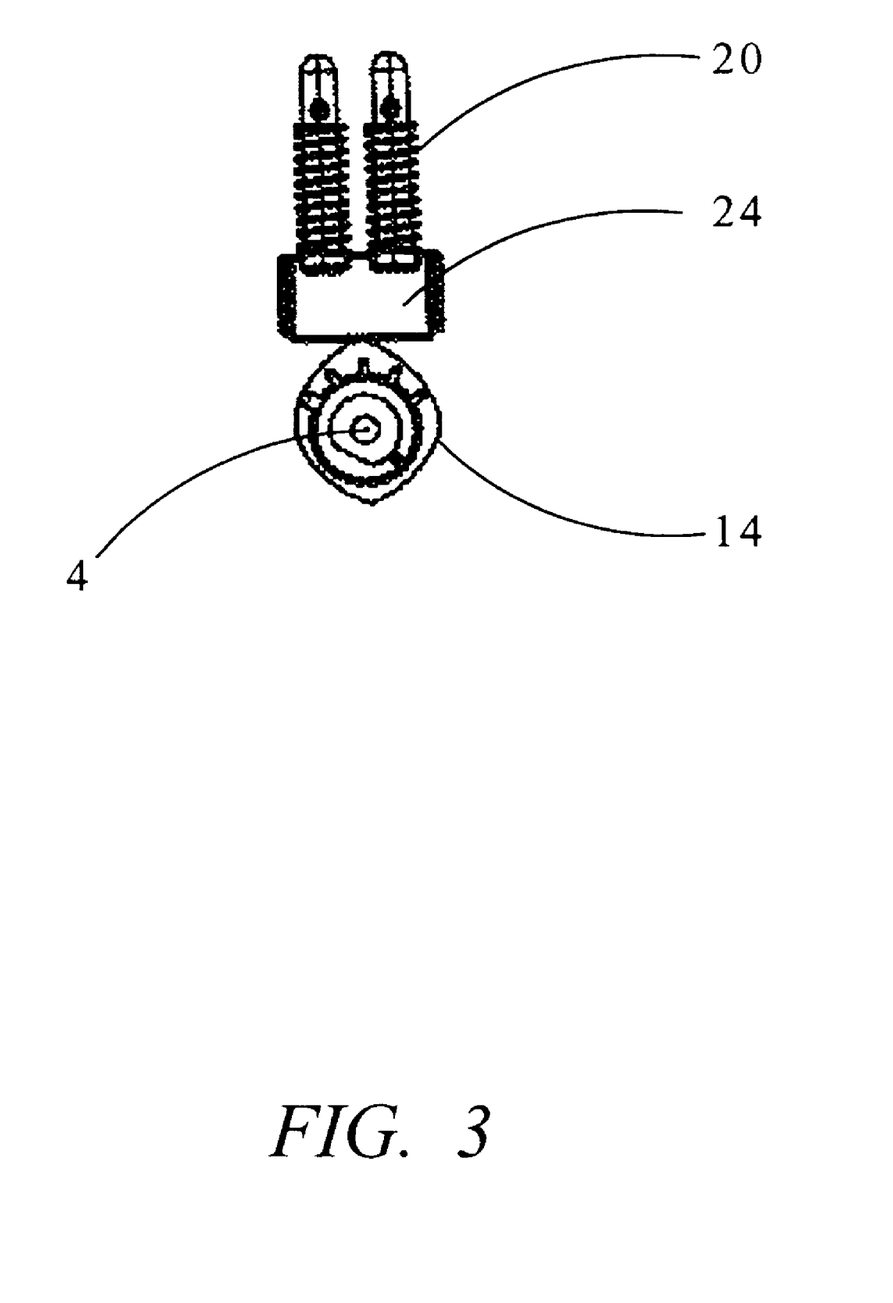
FIG. 3 is a side view of the compensation cam in FIG. 2.

As best seen in FIG. 1, the infusion pump system 1 of the invention comprises a stepper motor 2 which is connected to a cam shaft 4 via a reduction gear set 6. The stepper motor 2 drives the cam shaft 4 with several cams 8 positioned thereon at various spaced positions around the circumference of the shaft 4. These cams 8 connectively engage with follower fingers 10 that compress various portions of an intravenous (IV) drip tubing 12 running parallel to the cam shaft 4. A intravenous (IV) drip bag 22 contains fluid which flows to the patient via the tube 12. The tube 12 is manually placed into the mechanism via a capture plate or door 16. The result being that IV fluid in the tubing 12 is forced through the pump 1 at precisely controlled rates which are directly related to the stepper motor step rate.

Figure 4:
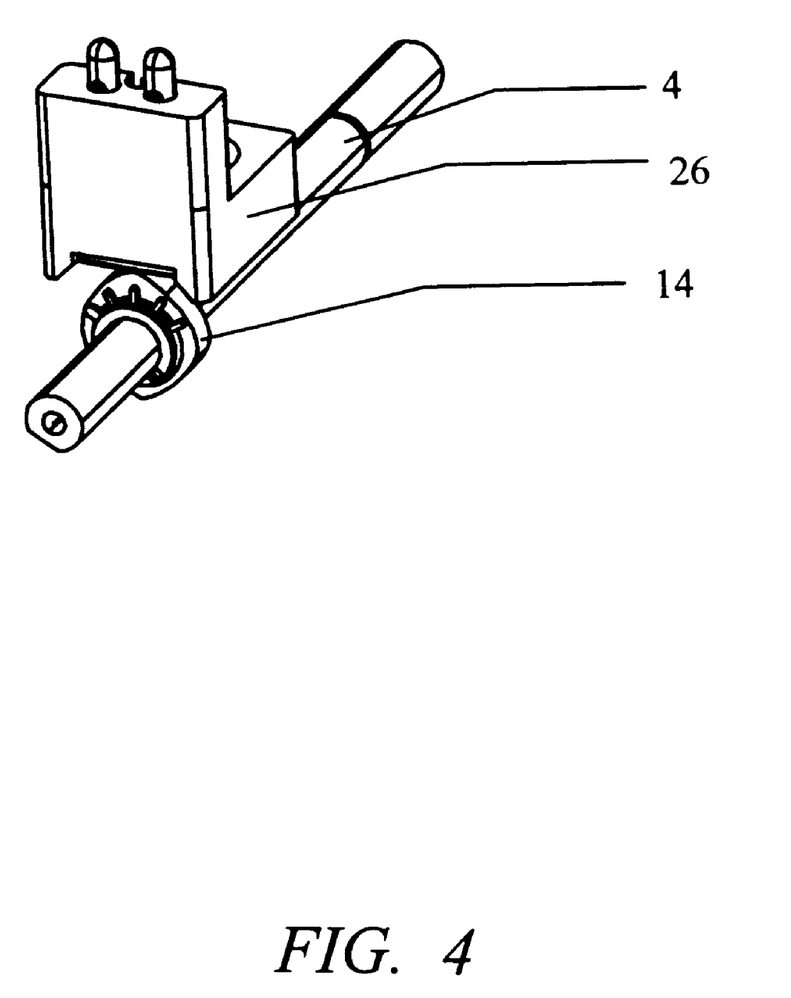
FIG. 4 is a perspective view of the compensation cam in FIG. 2, with the housing in place.
Figure 5:
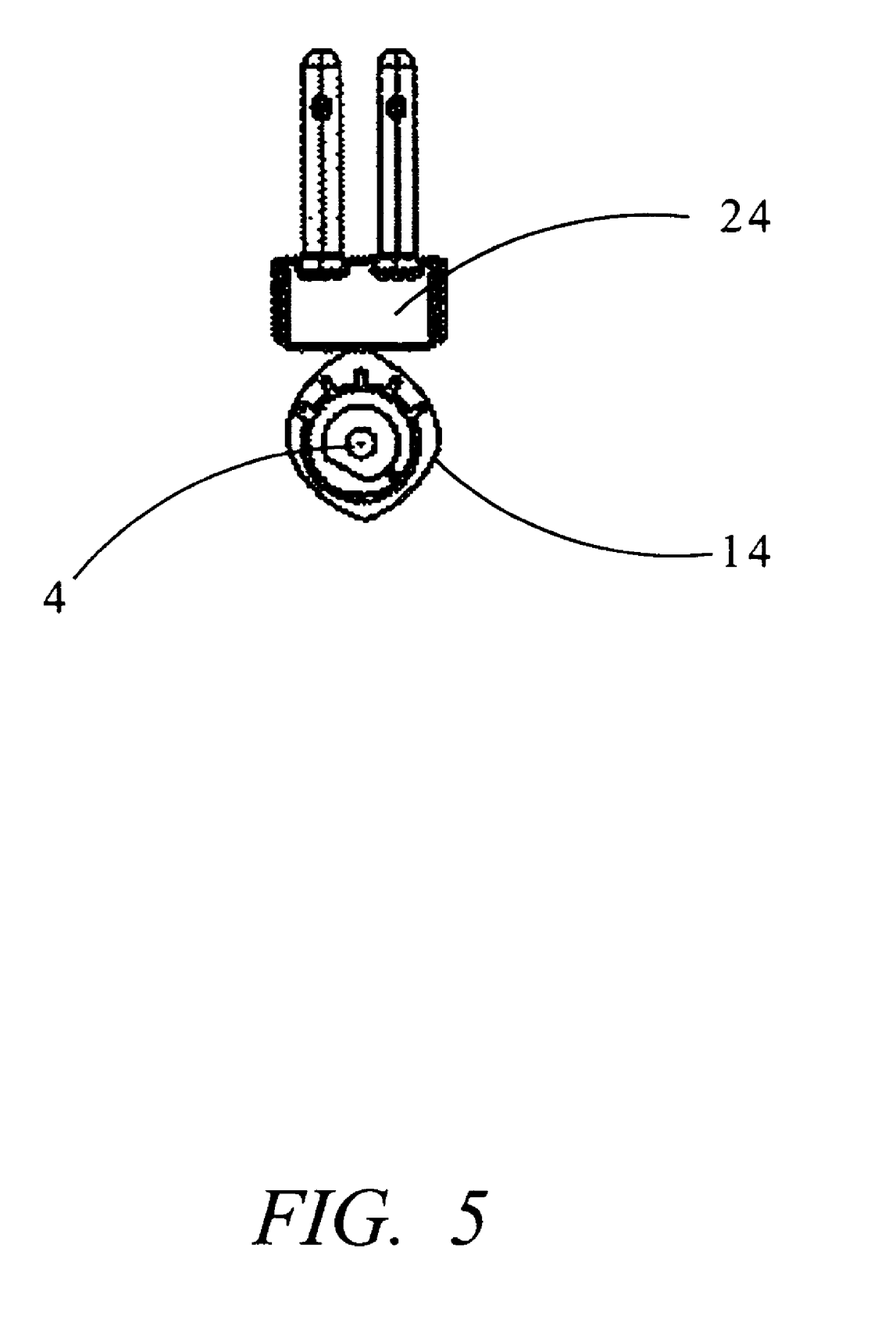
FIG. 5 is a side view of the compensation cam in FIG. 2, without the springs in place.

FIGS. 1 to 5 show an embodiment of a torque compensation system according to the present invention. The torque compensation system comprises of at least one additional cam, compensation cam 14, positioned on the cam shaft 4. Compensation cam 14 is provided with lobes and valleys on the surface thereof, which correspond to opposing lobes and valleys of the other cams 8. The compensation cam 14 is in turn operatively connected to a compensation cam follower 24, as best seen in FIGS. 2–5. The compensation cam 14 compresses, through the compensation cam follower 24, a mechanical spring 20 or like energy storage element. A housing 26 covers the compensation cam follower 24 and the spring 20, as best seen in FIG. 4. When the compensation cam follower 24 engages the rear side of a lobe, on the compensation cam's surface, the spring force is applied to the cam shaft 4 effectively assisting the motor 2 while it is working against a rising follower finger 10. The result is that the motor 2 experiences much lower amplitude changes in torque loading. The compensation cam 14 slightly raises the overall average torque loading on the motor 2 due to its contribution of some function to the system. This increased average torque loading is however not significant when compared to the benefits gained by the compensation cam 14.

The compensation cam follower 24 provides an additional benefit in burst mode. Burst mode is when a burst of motor steps are given to the motor followed by a variable delay time during which the motor is not moving and is in "hold". Where the motor is between bursts, in hold, some current flow remains in the motor coils to prevent the motor from being back driven (or forward driven) by the mechanism. The compensation cam reduces the level of hold current needed since the forward and back torque seen by the motor is significantly reduced. The compensation cam also provides a benefit while bursting in that the power needed is lower since the overall torque load is lower.

Figure 6:
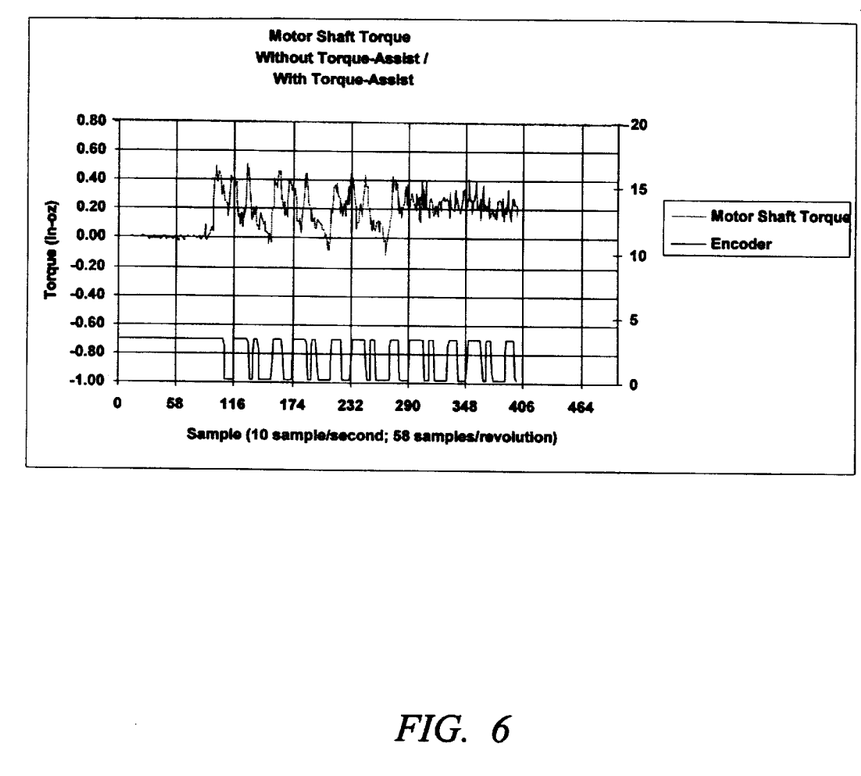
FIG. 6 is a graph of the motor torque versus the rotation of the cam shaft.

FIG. 6 shows the results of a test which was conducted to illustrate the torque compensation system of the invention. Torque on the motor shaft is plotted against the rotation of the cam shaft (58 samples per revolution). Between approximately sample 90 and sample 290, it can be seen that the torque load on the stepper motor severely fluctuates during the rotation of the cam shaft. The torque on the cam shaft varies from approximately–0,1 to 0,5 in-oz. The torque loading levels and the rates of change of torque loading vary with pumping rate and with other factors such as backpressure accumulated in the tubing when small orifice needles are used. In order to meet the demands of the fluctuating torque load and to assure that the motor does not stall under any operating conditions the stepper motor current levels are typically fixed by selecting an "upper power level" for each pumping rate. This requires the "upper power level" to be set for the highest torque level that the stepper motor is exposed to. This set "upper power level" results in excess power being applied to the stepper motor during periods that have low torque, leading to power wastage. By reducing overall torque on the system, a lower "upper power level" may be selected for each pumping rate, thereby reducing overall power consumption. The "upper power level" setting in burst mode can also be set to a lower value.

Approximately between sample 290 and sample 400, the torque compensation cam system was engaged. The effects of the torque compensation cam system can be seen as there is a noticeable reduction in both motor shaft torque loading and fluctuation. Furthermore, it can be seen that the "upper power level" can be set to a significantly lower level than that which would have to be set if there were no torque compensation cam.

An added advantage of the compensation cam, is that in reducing the amplitude of the peak to peak torque load profile, an automatic reduction of rate of change of torque loading occurs. In an alternative embodiment, the compensation cam is designed so as to only counteract the peaks leaving the rate of rise of torque the same between the reduced peaks.

Figure 7:
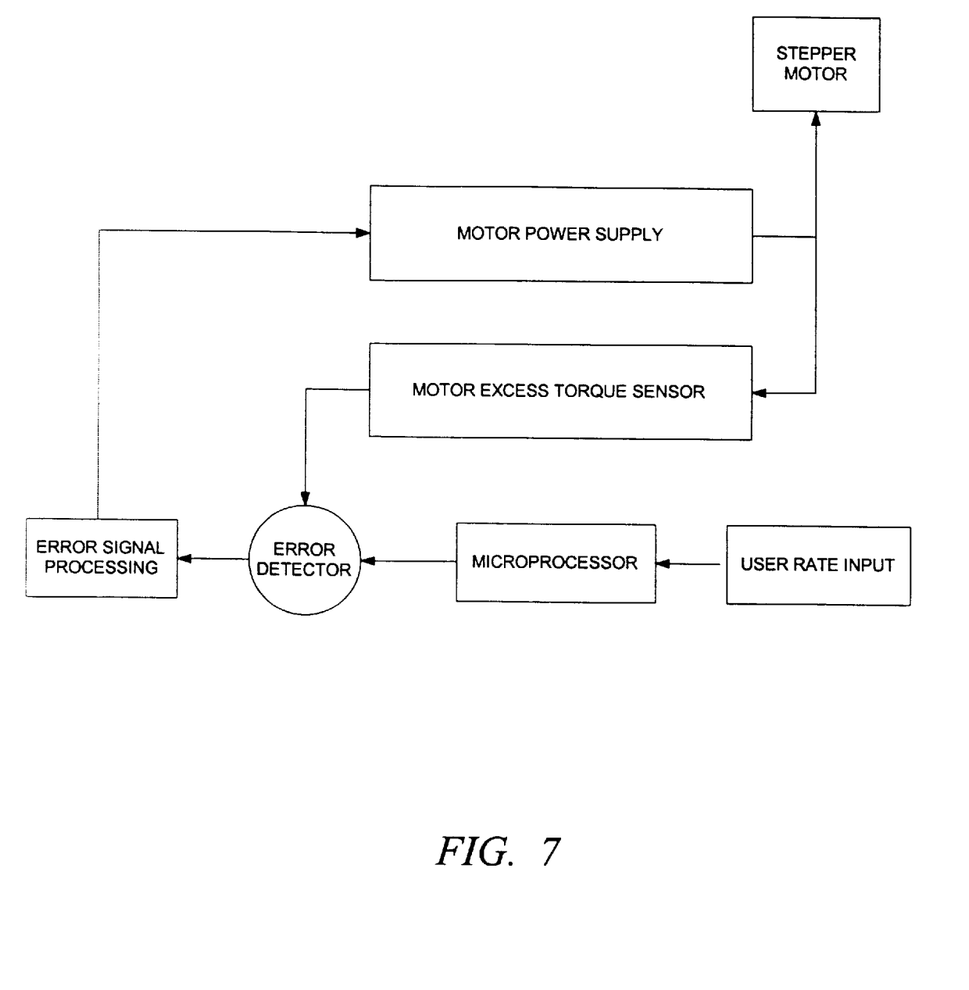
FIG. 7 is a schematic block diagram of a feedback control system according to another embodiment of the invention.

FIG. 7 shows a feedback control system according to another embodiment of the invention. The feedback control system detects the excess power in the system caused by changes in loading on the motor by means of a motor excess torque sensor. The sensor feeds a signal into an error detector, which compares the actual excess power with a predetermined desired power. The predetermined desired power is set by software control, for example in a microprocessor, for a specific pumping rate set by the user. The error detector then processes the excess power and desired power signals, and feeds the result to a variable power supply which in turn adjusts the power supplied to the motor.

The stepper motor used to rotate the cam, can be of any number of phases, but preferably is a five phase motor. The output voltage of the motor power supply, which applies power to the phases of the stepper motor in sequence to cause the rotor to turn, is adjusted such that minimum power is applied. The motor excess torque sensor senses the magnitude of the current measured for the motor phases. As load increases on the motor, the current increases, resulting in an error signal which is summed in the error detector with a preset signal from a microprocessor, resulting in a fixed excess torque added to an optimum torque. A table is held in the memory of the microprocessor as a function of rate. This is done such that there will always be more torque available by the motor to account for some load changes without stalling. This excess torque is determined empirically by measuring required torque and using the maximum deviations as the excess torque multiplied by a safety factor, such as for example a safety factor of two (2). The error signal processing in this embodiment can either be a classic PID (proportional integral differential) process using either analog parts or implemented in the microprocessor, or a PI (proportional integral) system, where the direct signal is conditioned and added to the integral of the error signal, the result being transferred to the power supply of the motor.

In another embodiment, the current slope of the motor is dissected into N parts for each phase and slope change resulting from motor load variations and is used to create the motor excess torque signal. As an example, with N equal 2, the current waveform is divided into two parts, the first part of the waveform is compared with the second half by integrating the signals, inverting the second half and summing them, resulting in an error signal measuring excess current which occurs when the motor rotor has completed its step.

In yet another embodiment, the pump can update the excess torque table based on experiencing motor stall events. Motor stall is detected using an encoder wheel, which is used to count revolutions and parts of revolutions of the pump camshaft. When missing steps are detected, the table can be updated to assure no stall conditions. This is used to counter wear, increased friction due to dirt or any other condition that would increase torque.

The variable power supply comprises of a variable output voltage switching power supply. The voltage from the variable power supply is fed to the motor driver "H" bridge circuitry to drive the stepper motor phases as required. Control logic generates phase signals as required by the stepper motor at a user programmed rate. A low value resistor is placed between the motor and ground which senses motor current. The voltage developed across this resistor is amplified and sent into a peak detector. The output of the peak detector is buffered (for drive capability) and sent to the error detector. The error detector is an op amp that responds with high gain to a difference between the peak detected motor current signal and the control input. The result of this (the error signal) is inverted and filtered to give an average error signal to the motor power supply voltage input. The motor power supply voltage is therefore directly related to the average error signal.

Furthermore, software controlled switches allow the feedback loop to be disabled for very low pumping rates where burst mode is used. In burst mode, the variable motor power supply is directly controlled by software at a fixed voltage independent of rate, as the only thing that determines pumping rate in burst mode is the delay time between bursts. All bursts are at the same rate and for the same number of steps. In the preferred application, if no delay time was left between bursts, the pumping rate would be approximately 120 milliliters per hour. Burst mode is generally not used at rates above 40 milliliters per hour.

Thus, according to the invention, the "upper power level" can be set (under software control from a look-up table or by some other method) to a single low value for each pumping rate. During pumping, the feedback control loop adjusts the power applied to the motor as needed to keep the excess power output constant irrespective of torque load fluctuation.

At faster pumping rates (above 40ml/hr in the preferred application) the feedback loop is activated to dynamically adjust the motor power supply voltage as needed to keep the motor current peaks essentially constant. The effect of torque loading change is that, for a given motor power supply voltage, the current will ramp up in the motor during each step at a different rate. When the torque loading is less, the current ramps up faster. Therefore the peak detector sees this higher peak current and the response is to lower the motor voltage. The net result being that the motor peak current is kept very constant under varying loading conditions. The peak current reached is proportional to the excess motor torque output beyond that which is needed by the mechanism. Therefore, the control input to the loop (under software control which, in the preferred application, is a constant value for any given pumping rate) is a value that is representative of the amount of excess torque output from the motor that provides a margin of safety against motor stall. (The motor will stall if the torque load exceeds the output torque available from the motor.)

The feedback loop needs some margin of excess power because there is a finite time required for the loop to sense an increase in torque loading and for the motor power supply to respond with an increase in its output voltage. For closed loop operation, peak torque levels are not specifically the cause of stall, for if these peak levels are arrived at slowly, the feedback loop can respond over a wide range of loads. It is the "rate of rise of torque" loading that will cause stall. An instantaneous step of added torque load that is only slightly higher than the margin given by the control input, will cause stall if the loop has no time to respond.

The power reduction system, consisting of a combination of both the feedback control system and the torque compensation cam system, allows the motor power to be finely tuned, eliminating excess power and reducing overall power consumption. An added benefit of the torque compensation system is a significant reduction of both the pump audible noise and vibration.

The foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A peristaltic pump, comprising:
   a drive means;
   a cam shaft driven by said drive means;
   a plurality of cams positioned at spaced intervals around the circumference of said cam shaft;
   a plurality of elongate fingers cooperating with said cams, said fingers capable of at least partly occluding an intravenous drip tube at multiple points along said tube's path; and
   a torque compensation system, including:
      at least one torque compensation cam positioned on said cam shaft;
      at least one torque compensation cam follower operatively connected to said torque compensation cam; and
      an energy storage element operatively connected to said torque compensation cam follower, which forcibly engages said torque compensation cam follower against said torque compensation cam,
   such that in use said torque compensation system decreases torque produced at said drive means thus reducing overall power consumption of said pump.

2. A peristaltic pump according to claim 1, wherein said drive means comprises:

a motor;

a reduction gear set connected to said motor; and a power supply.

3. A peristaltic pump according to claim 2, wherein said motor is a direct current operated stepper motor, capable of operating at a fixed rotational rate independent of loading.

4. A peristaltic pump according to claim 3, wherein said energy storage element is a mechanical spring.

5. A peristaltic pump, comprising:

a drive means;

a cam shaft driven by said drive means;

a plurality of cams positioned at spaced intervals around the circumference of said cam shaft;

a plurality of elongate fingers cooperating with said cams, said fingers capable of at least partly occluding an intravenous drip tube at multiple points along said tube's path; and a power feedback control system, further comprising:
   a variable output power supply, which controls power supplied to said drive means;
   a transducer for measuring excess power at said drive means; and
   a controller, capable of dynamically adjusting said variable output power supply by processing the measured excess power and a predetermined desired power, such that in use said power feedback control system optimally adjusts the power supplied to said drive means so as to reduce overall power consumption of said pump.

6. A peristaltic pump according to claim 5, wherein said controller comprises:

a voltage peak detector; and an error detector.

7. A peristaltic pump according to claim 6, wherein said error detector comprises an operational amplifier.

8. A peristaltic pump according to claim 7, wherein said predetermined desired power is set by a user of said pump, for each specific pumping rate.

9. A peristaltic pump according to claim 8, wherein said pump further comprises:

a torque compensation system comprising:
   at least one torque compensation cam positioned on said cam shaft;
   at least one torque compensation cam follower operatively connected to said torque compensation cam; and
   an energy storage element operatively connected to said torque compensation cam follower, which forcibly engages said torque compensation cam follower against said torque compensation cam, such that in use said torque compensation system decreases torque produced at said drive means thus reducing overall power consumption of the pump.

10. A peristaltic pump, comprising:

a stepper motor;

a cam shaft driven by said motor;

a plurality of cams positioned at spaced intervals around the circumference of said cam shaft;

a plurality of elongate fingers cooperating with said cams, said fingers capable of at least partly occluding an intravenous drip tube at multiple points along said tube's path; and a torque compensation system, further comprising:
   at least one torque compensation cam positioned on said cam shaft;
   at least one torque compensation cam follower operatively connected to said torque compensation cam; and
   an energy storage element operatively connected to said torque compensation cam follower, which forcibly engages said torque compensation cam follower against said torque compensation cam; and a power feedback control system, further comprising:
   a variable output power supply, which controls power supplied to said stepper motor;
   a transducer for measuring excess power at said drive means; and
   a controller, capable of dynamically adjusting said variable output power supply by processing the measured excess power and a predetermined desired power, such that in use said power feedback control system optimally adjusts the power supplied to said power source and said torque compensation system decreases torque produced at said motor, the combination of said power feedback control system and said torque compensation system, reducing overall power consumption of said pump.

11. A method of controlling the operation of a peristaltic infusion pump, in order to reduce said pump's power consumption, comprising the steps of:

determining a desired power value;

measuring an excess power value caused by torque loading on a drive means;

processing said predetermined desired power value and said excess power value to form a new value; and adjusting power supplied to said drive means in accordance with said new value.

12. A method according to claim 11, wherein said method further comprises the steps of:

providing at least one torque compensation cam positioned on said cam shaft;

furnishing at least one torque compensation cam follower operatively connected to said torque compensation cam; and supplying an energy storage element operatively connected to said torque compensation cam, which forcibly engages said torque compensation cam follower against said torque compensation cam to decrease any torque produced at said drive means.

* * * * *